United States Patent [19]

Smiley

[11] 4,287,134

[45] Sep. 1, 1981

[54] PURIFICATION OF ACETONITRILE BY CAUSTIC EXTRACTION

[75] Inventor: Robert A. Smiley, Wilmington, Del.

[73] Assignee: E. I. Du Pont de Nemours and Company, Wilmington, Del.

[21] Appl. No.: 163,100

[22] Filed: Jun. 26, 1980

[51] Int. Cl.$^3$ ............... C07C 121/18; G07C 121/14
[52] U.S. Cl. ...................... 260/465.1; 260/465.3
[58] Field of Search ...................... 260/465.1

[56] References Cited

U.S. PATENT DOCUMENTS

| | | | |
|---|---|---|---|
| 2,453,472 | 11/1948 | Teter et al. | 260/465.1 |
| 3,203,974 | 8/1965 | Sobel et al. | 260/465.1 |
| 3,328,458 | 6/1967 | Iappelli et al. | 260/465.1 |
| 3,451,899 | 6/1969 | Sheely | 260/465.1 X |
| 4,119,497 | 10/1978 | Ocampo et al. | 203/29 |

FOREIGN PATENT DOCUMENTS 1431919  11/1975  France .

OTHER PUBLICATIONS

Coetzee, Pure & Applied Chemistry, 13, (1966), pp. 429–435.

*Primary Examiner*—Joseph Paul Brust

[57] ABSTRACT

Process for removing water and HCN contained in acetonitrile by contacting the acetonitrile with concentrated caustic in one or more stages.

3 Claims, No Drawings

PURIFICATION OF ACETONITRILE BY CAUSTIC EXTRACTION

BACKGROUND OF THE INVENTION

1. Field of the Invention

The present invention relates to the purification of acetonitrile and particularly to the removal of hydrogen cyanide and water from acetonitrile by contacting the nitrile in one or more steps with a concentrated alkali metal hydroxide.

2. Description of the Prior Art

Numerous processes have been disclosed for the purification of acetonitrile many depending upon the desired use of the acetonitrile. U.S. Pat. No. 3,328,458 issued on June 27, 1967 discloses the removal of water and hydrogen cyanide from acetonitrile by first contacting the nitrile with a drying agent such as calcium chloride, sodium sulfate or alumina and a compound which may be used in combination with the aforesaid drying agent to produce a soluble cyanide salt such as copper acetate or silver nitrate. U.S. Pat. No. 3,203,974 issued on Aug. 31, 1965 discloses the removal of pyridine from acetonitrile by contacting the nitrile with acids and acid anhydrides which are formed by the combination of oxygen and a normally solid element of Groups III, IV and V of the Periodic Table, e.g., boric acid, phosphoric acid and stanic acid.

An elaborate technique for azeotropic distillation of acetonitrile to remove water, hydrogen cyanide, acrylonitrile, acetone and higher boiling nitriles is disclosed in U.S. Pat. No. 3,451,899 issued on June 24, 1969. Acetonitrile purification by reacting the crude acetonitrile with alkali metal and ammonium hydroxide, ammonia and aliphatic amines at a temperature between 50°–212° F. to form a reaction mixture in which the hydrogen cyanide and acrylonitrile transform into compounds of higher molecular weight and the resultant material fractionally distilled to recover pure acetonitrile is disclosed in U.S. Pat. No. 4,119,497 issued on Oct. 10, 1978.

Acetonitrile can be dehydrated by the addition of methylene chloride, subjecting the thus formed mixture to stratification to separate an aqueous upper layer, and fractionally distilling the water in the methylene chloride from the lower layer as a binary azeotrope according to the teachings of U.S. Pat. No. 2,453,472 issued on Nov. 9, 1948.

Alkaline media, e.g., sodium hydroxide, have been employed as a part of purification processes. East German Pat. No. 110,489 published on Dec. 20, 1974 combines discontinuous azeotropic distillation with acrylonitrile to dry the acetonitrile followed by heating the distillate in an alkaline medium up to 90° C. to permit decomposition of impurities and further distillation. Acetonitrile water azeotrope is taken overhead and decomposition products of acrylonitrile and hydrocyanic acid are removed in the tails.

Titratable cyanides and acrylonitrile in acetonitrile have been converted to sodium cyanides and succinonitrile respectively by the addition of sodium hydroxide followed by the addition of ferrous sulfate to convert sodium cyanide into sodium ferrocyanide. Distillation is then used to recover acetonitrile having a low cyanide content (Japanese Pat. No. 7235416 published on Mar. 23, 1962). Dilute sodium hydroxide has been disclosed as a catalyst for the cyanoethylation of acrylonitrile contained in acetonitrile, e.g., in French Pat. No. 1,431,919 issued on Mar. 18, 1966.

It is also known that concentrated caustic causes nitriles to hydrolize [Kirk, Othmer, Encyclopedia of Chemical Technology, Vol. 9, pp. 356-7 (19)] which reaction has been taught to be undesirable in the purification of acetonitrile [Pure & Applied Chemistry, 13 429–431 (1966)].

SUMMARY OF THE INVENTION

A process for the purification of acetonitrile and particularly for the removal of water and hydrogen cyanide therefrom which process comprises contacting crude acetonitrile initially containing water and hydrogen cyanide with an aqueous solution consisting essentially of 25–60% by weight of an alkali metal hydroxide in one or more stages and thereafter recovering acetonitrile containing essentially no hydrogen cyanide and having a decreased amount of water relative to the crude acetonitrile. It is preferred to conduct the process of the present invention at a temperature in the range 25°–82.5° C. and more preferably about ambient temperature using sodium hydroxide as the alkali metal hydroxide.

DETAILED DESCRIPTION OF THE INVENTION

A typical stream to which the process of the present invention may be applied is a liquid stream of predominately acetonitrile containing by weight based upon the weight of the stream 1–30% and usually 16–24% of water and 1,000–20,000 ppm of hydrogen cyanide along with some acrylonitrile and trace amounts of other organics. Such a stream is obtained from the purification portion of a process for producing acrylonitrile by the ammoxidation of propylene.

The process of the present invention can be conducted over a wide range of temperatures. Preferred temperatures are those of approximately ambient but can vary up to 82.5° C. which is the boiling point of the acetonitrile. Lower temperatures consistent with satisfactory removal of hydrogen cyanide and reduction in water level are preferred to minimize hydrolysis of the nitrile which can occur at elevated temperatures.

The method of contacting the crude acetonitrile with the concentrated caustic is not critical to the present invention and it is believed apparent to one skilled in the art, for example, the components may be mixed under gentle or severe agitation. After thorough contacting the resultant material is permitted to form an organic and aqueous phase and the acetonitrile is recovered as the organic phase.

The alkali metal hydroxides which are operable in the present invention include sodium and potassium hydroxide. These hydroxides must be in concentrated form in order to achieve the results herein realized. Aqueous solutions containing 25–60% by weight of an alkali metal hydroxide are generally satisfactory for the practice of the present invention. Aqueous solutions containing about 50% by weight of the alkali metal hydroxide are preferred.

The ratio of the volume of aqueous alkali metal hydroxide to the volume of the typical stream hereinabove described can vary from 1:1–1:50 but is preferably maintained in the range of 1:1–1:10 for single staged contact and in the range of 1:1–1:20 for each stage in multiple stages.

The following examples are presented to illustrate but not to restrict the present invention. Parts and percentages are by weight unless otherwise specified.

EXAMPLE 1

An acetonitrile water solution containing free hydrogen cyanide having the following composition was prepared:

| Compound | % |
|---|---|
| Water | 17.7 |
| HCN | 1.1 |
| Acetonitrile | 80.7 |
| Acrylonitrile | 0.4* |
| Propionitrile | 0.1* |

Approximately 1010 parts of the above solution were contacted by shaking with 100 parts of a 50% aqueous sodium hydroxide solution at room temperature for approximately 2 minutes following which the phases were permitted to separate at room temperature. Approximately 239 parts of aqeuous phase and 865 parts of organic phase were recovered. The organic phase had the following composition:

| Compound | % |
|---|---|
| Water | 5.7 |
| HCN | Not Detectable |
| Acetonitrile | 93.8 |
| Acrylonitrile | 0.4* |
| Propionitrile | 0.1* |

*Approximate

The foregoing demonstrates that one extraction removed essentially all of the hydrogen cyanide and 76% of the water.

EXAMPLE 2

A solution was prepared by combining 60 parts of water and 240 parts of acetonitrile at room temperature. This solution was extracted four times with a 50% aqeuous sodium hydroxide solution according to the procedure of Example 1 in the amounts and with the results set forth in Table I:

TABLE I

| Extraction No. | Parts of 50% NaOH | Extract Parts | Analysis of ACN Layer (%) | |
|---|---|---|---|---|
| | | | Water | Acetonitrile |
| 1 | 30 | 72 | 7.4 | 92.5 |
| 2 | 26 | 38 | 2.6 | 97.4 |
| 3 | 25 | 30 | 1.1 | 98.9 |
| 4 | 25 | 25 | 0.7 | 99.3 |

The foregoing amounts to the removal of 98% of the water initially present.

I claim:

1. A process for removing water and hydrogen cyanide from a crude solution containing acetonitrile, 16-24% by weight water and 1000-20,000 ppm hydrogen cyanide which comprises thoroughly contacting 1-50 parts by volume of said crude solution with 1 part by volume based upon the volume of said crude solution of an aqueous solution consisting essentially of 25-60% by weight of an alkali metal hydroxide selected from the class consisting of sodium hydroxide, potassium hydroxide and mixtures thereof at a temperature in the range of 25°-82.5° C., permitting the thus formed mixture to form an organic and aqueous phase, and recovering the organic phase comprising acetonitrile containing essentially no hydrogen cyanide and having decreased amount of water relative to said crude solution.

2. The process of claim 1 wherein the alkali metal hydroxide is sodium hydroxide.

3. The process of claim 1 wherein said contacting is conducted in a plurality of stages.

* * * * *